United States Patent [19]

Aoki et al.

[11] Patent Number: 4,690,704
[45] Date of Patent: Sep. 1, 1987

[54] DERIVATIVES OF TETRAHYDROBENZOTHIAZOLE AND HERBICIDAL COMPOSITIONS CONTAINING THE SAME AS AN ACTIVE INGREDIENT

[75] Inventors: Katsumichi Aoki; Takafumi Shida; Hideo Arabori; Satoru Kumazawa; Susumu Shimizue; Takeo Watanave; Yohichi Kanda; Keigo Satake; Shiro Yamazaki; Hiroyasu Shinkawa, all of Iwaki, Japan; Tsuneaki Chida, Greenbelt, Md.

[73] Assignee: Kureha Kagaku Kogyo Kabushiki Kaisha, Tokyo, Japan

[21] Appl. No.: 820,278

[22] Filed: Jan. 17, 1986

Related U.S. Application Data

[63] Continuation-in-part of Ser. No. 597,451, Apr. 6, 1984, Pat. No. 4,624,697.

[30] Foreign Application Priority Data

Apr. 8, 1983 [JP] Japan ............................... 58-61924

[51] Int. Cl.$^4$ ................... C07D 417/04; A01N 47/38
[52] U.S. Cl. ........................................ 71/90; 548/132; 548/162
[58] Field of Search .................... 548/132, 102; 71/90

[56] References Cited

U.S. PATENT DOCUMENTS 4,481,077 11/1984 Aoki ........................................ 71/90

Primary Examiner—Robert Gerstl
Attorney, Agent, or Firm—Austin R. Miller

[57] ABSTRACT

Disclosed herein are a derivative of tetrahydrobenzothiazole represented by the formula (I):

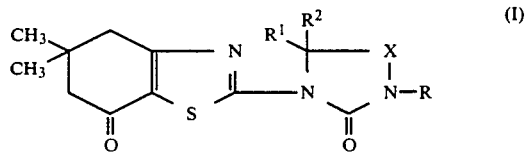

wherein R represents a methyl group or ethyl group; $R^1$ represents a hydrogen atom, a hydroxyl group, methoxy group or O== together with $R^2$; $R^2$ represents a hydrogen atom or O== together with $R^1$; and X represents a methylene group, hydroxymethylene group, carbonyl group or —O— with the proviso that R is not a methyl group when (1) $R^1$ represents a hydroxyl group or methoxy group and X represents a methylene group or hydroxymethylene group or (2) $R^2$ represents =O together with $R^1$ and X represents a carbonyl group, and a herbicidal composition containing the same as an active ingredient.

2 Claims, 11 Drawing Figures

DERIVATIVES OF TETRAHYDROBENZOTHIAZOLE AND HERBICIDAL COMPOSITIONS CONTAINING THE SAME AS AN ACTIVE INGREDIENT

CROSS-REFERENCE TO RELATED APPLICATION

The present application is a continuation-in-part application of U.S. patent application Ser. No. 597,451 filed on Apr. 6, 1984 now U.S. Pat. No. 4,624,697.

SUMMARY OF THE INVENTION

In a first aspect of the present invention, there is provided a derivative of tetrahydrobenzothiazole represented by the formula (I):

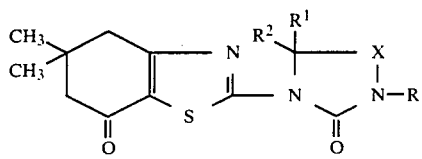

wherein R represents a methyl group or ethyl group; $R^1$ represents a hydrogen atom, a hydroxyl group, methoxy group or =O together with $R^2$; $R^2$ represents a hydrogen atom or =O together with $R^1$ and X represents a methylene group, hydroxymethylene group, carbonyl group or —O— with the proviso that R is not a methyl group when (1) $R^1$ represents a hydroxyl group or methoxy group and X represents a methylene group or hydroxymethylene group or (2) $R^2$ represents =O together with $R^1$ and X represents a carbonyl group.

In a second aspect of the present invention, there is provided a herbicidal composition comprising as an active ingredient a herbicidally effective amount of at least one derivative of tetrahydrobenzothiazole represented by the formula (I), and a diluent therefor.

BRIEF EXPLANATION OF THE DRAWINGS

In the attached drawing.

DETAILED DESCRIPTION OF THE INVENTION

Figure 1:
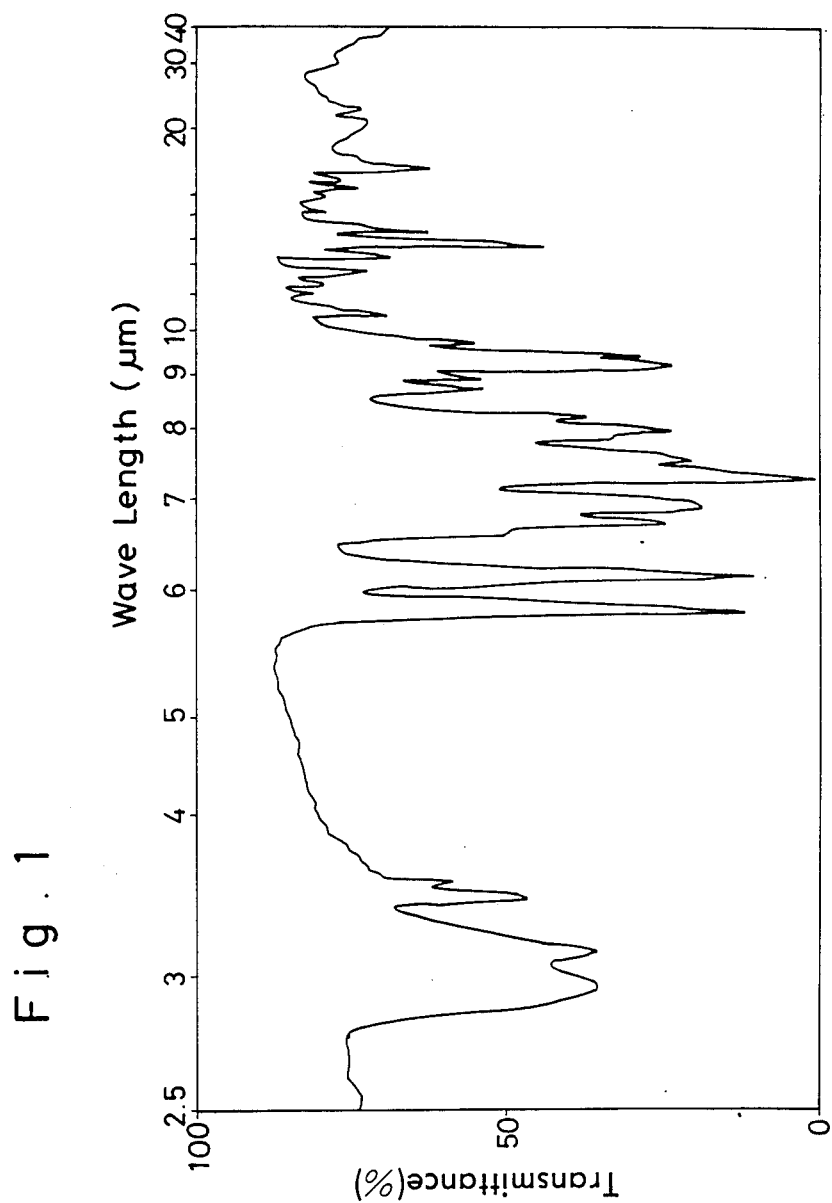
FIGS. 1 to 11 show the infrared absorption spectra of Compounds Nos. 1 to 11 according to the present invention, respectively.

The present invention relates to a derivative of tetrahydrobenzothiazole represented by the formula (I):

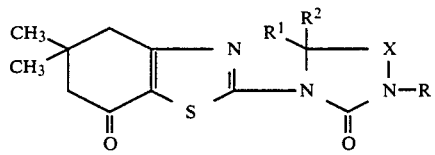

wherein R represents a methyl group or ethyl group; $R^1$ represents a hydrogen atom, a hydroxyl group, methoxy group or =O together with $R^2$; $R^2$ represents a hydrogen atom or =O together with $R^1$ and X represents a methylene group, hydroxymethylene group, carbonyl group or —O— with the proviso that R is not a methyl group when (1) $R^1$ represents a hydroxyl group or methoxy group and X represents a methylene group or hydroxymethylene group or (2) $R^2$ represents =O together with $R^1$ and X represents a carbonyl group, and a herbicidal composition containing the same as an active ingredient.

The present inventors have studied for finding a compound showing an excellent activity in selectively controlling weeds such as *Echinochloa crus-galli*, *Poa annua*, *Cardamine flexuosa*, *Portulaca orelacea*, etc. without any phytotoxicity to crop plants such as rice, wheat, soybean and maize, and as a result, they have found that a derivative of tetrahydrobenzothiazole, represented by the formula (I) shows an excellent herbicidal activity for practically controlling the weeds, and have attained to the present invention.

The compounds represented by the formula (I) are novel compounds, and of course, the physiological properties of the compounds have never been known. According to the herbicidal tests consisting essentially of foliar application and soil treatment, the derivatives of tetrahydrobenzothiazole according to the present invention (hereinafter referred to as "the present compounds") show an excellent herbicidal activity on broad-leaved weeds, for instance, *Stellaria media*, *Cardamine flexuosa*, and *Portulaca oleracea*, Cyperaceous weeds, for instance, *Cyperus iria* and Gramineous weeds, for instance, those belonging to the genus Echinochloa and *Poa annua*, and particularly show strong herbicidal activity when applied on leaves and stems of these weeds.

The application is carried out on crop lands such as paddy fields, upland fields, orchards etc. and also on non-crop lands.

The compounds of the present invention represented by the formula (I) can be synthesized by various methods, for example, can be synthesized as follows.

In the case where a compound represented by the formula (II) is reacted with glyoxal, a compound represented by the formula (III) is obtained.

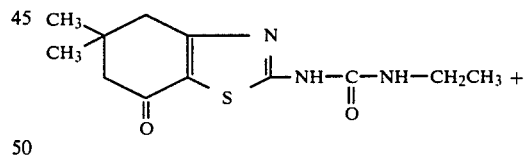

(II)

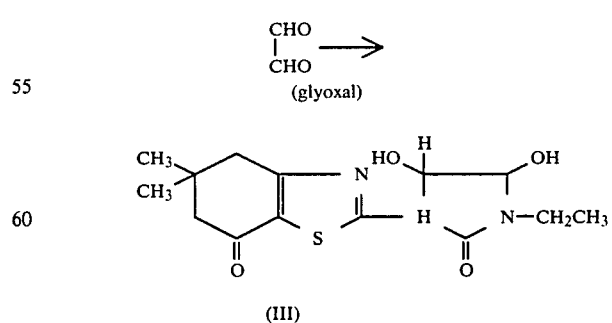

(III)

In the case where a compound represented by the formula (II) is reacted with oxayly chloride, a compound represented by the formula (IV) is obtained.

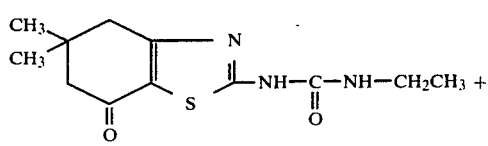

(II)

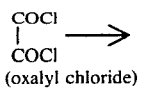

(oxalyl chloride)

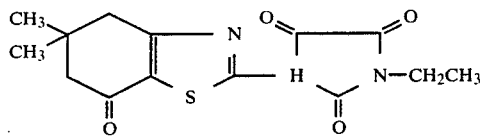

(IV)

In the case where a compound represented by the formula (II) is reacted with glyoxylic acid, a compound represented by the formula (V) is obtained.

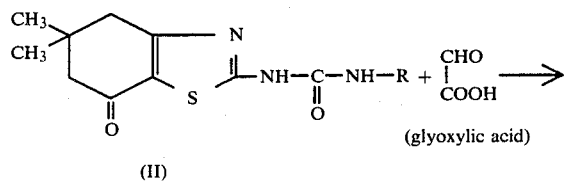

(II)

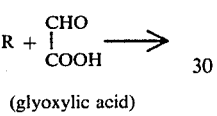

(glyoxylic acid)

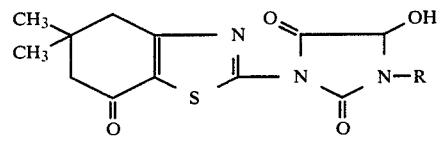

(V)

(wherein R represents a methyl group or ethyl group)

In the case where a compound represented by the formula (VI) is treated with aqueous diluted solution of mineral acid, a compound represented by the formula (VII) is obtained.

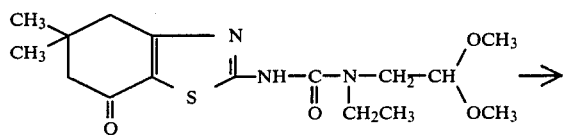

(VI)

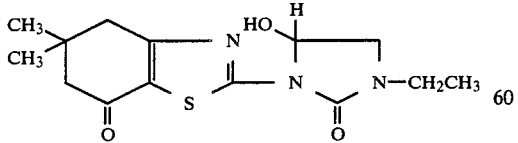

(VII)

Further, by heating the compound represented by the formula (VII) in methanol in the presence of an acid catalyst, a compound represented by the following formula is obtained.

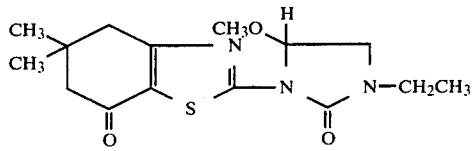

In the case where a compound represented by the formula (VIII) is reacted with phosgene or carbonyldiimidazole, a compound represented by the formula (IX) is obtained.

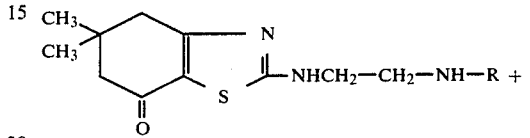

(VIII)

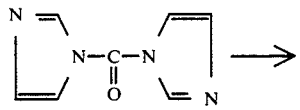

(carbonyldiimidazole)

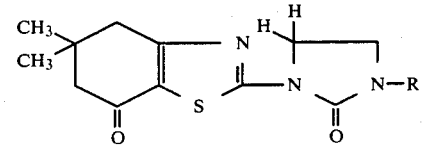

(IX)

(wherein R represents a methyl group or ethyl group)

In the case where a compound represented by the formula (X) is reacted with phosgene or carbonyldiimidazole, a compound represented by the formula (XI) is obtained.

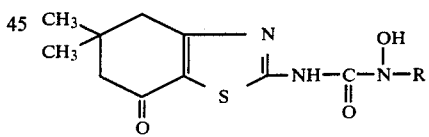

(X)

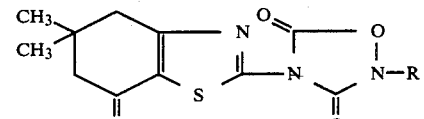

(XI)

(wherein R represents a methyl group or ethyl group)

In the case where a compound represented by the formula (XII) is reacted with an aqueous dilute solution of a mineral acid, a compound represented by the formula (XIII) is obtained.

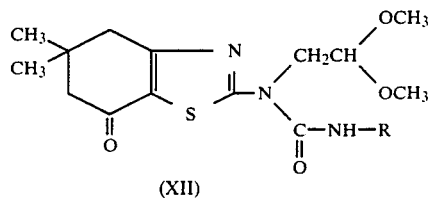

(XII)

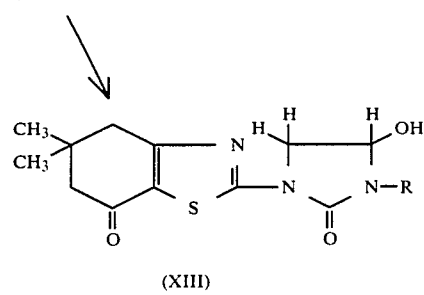

(XIII)

(wherein R represents a methyl group or ethyl group)

In the case where a compound represented by the formula (XIV) is reacted with acetic anhydride, a compound represented by the formula (XV) is obtained.

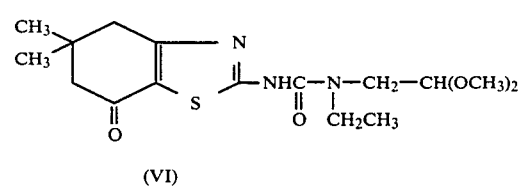

(XIV)

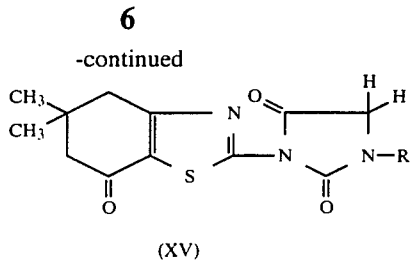

(XV)

(wherein R represents a methyl group or ethyl group)

The compounds represented by the formulae (II), (VI), (VIII), (X), (XII) and (XIV) may be preferably synthesized as follows.

The compound represented by the formula (II) is obtained by reacting ethyl isocyanate to a compound represented by the formula (XVI):

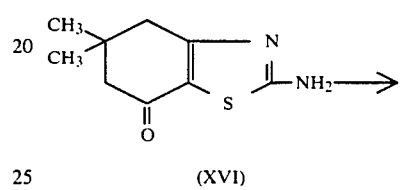

(XVI)

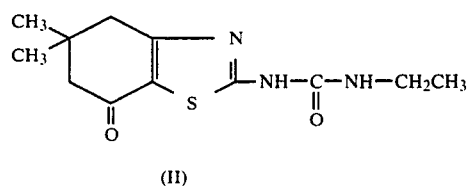

(II)

The compounds respectively represented by the formulae (VI), (X) and (XIV) are obtained by reacting a suitable amino compound to a compound represented by the formula (XVII) which is obtained by reacting phenyl chloroformate with a compound represented by the formula (XVI):

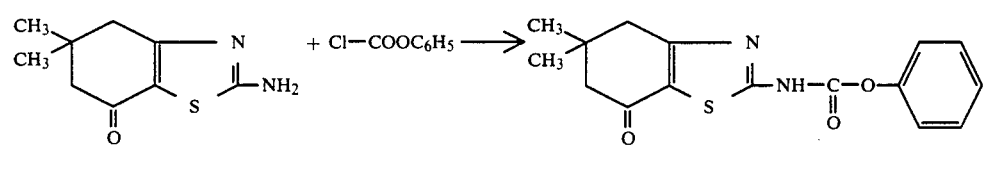

(XVI)          (XVII)

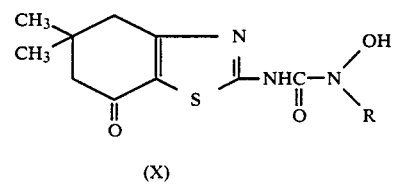

(VI)

(X)

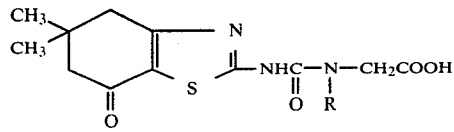

(XIV)

The compound represented by the formula (VIII) is obtained by substituting a chlorine atom in the compound represented by the formula (XVIII) with a suitable amino compound.

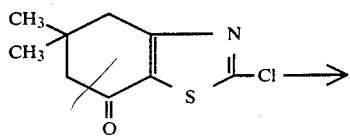

(XVIII)

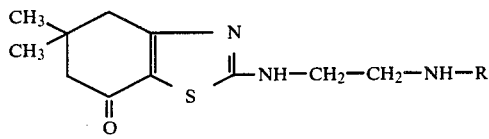

(VIII)

The compound represented by the formula (XII) is obtained by reacting methyl isocyanate or ethyl isocyanate with the compound represented by the formula (XIX) which is obtained by substituting a chlorine atom in the compound represented by the formula (XVIII) with a suitable amino compound.

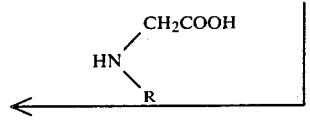

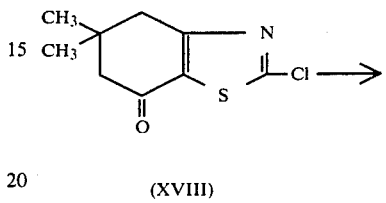

(XVIII)

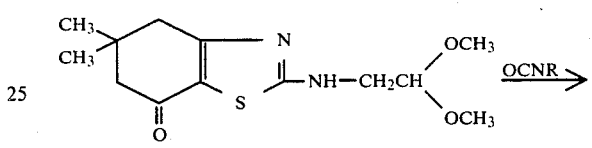

(XIX)

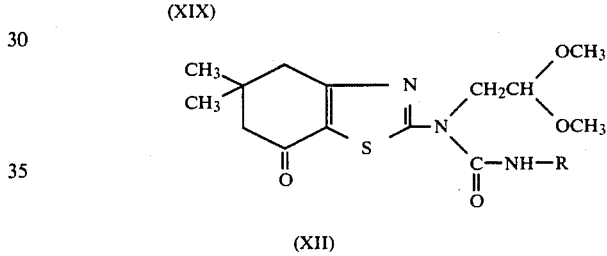

(XII)

The thus obtained compounds represented by the formula (I) are concretely shown in Table 1 together with the respective physical properties thereof.

TABLE 1

$$R^1 \underset{-N}{\overset{R^2}{\underset{|}{+}}} \underset{\underset{O}{\|}}{\overset{X}{\underset{|}{+}}} N-R$$

Figure 2:
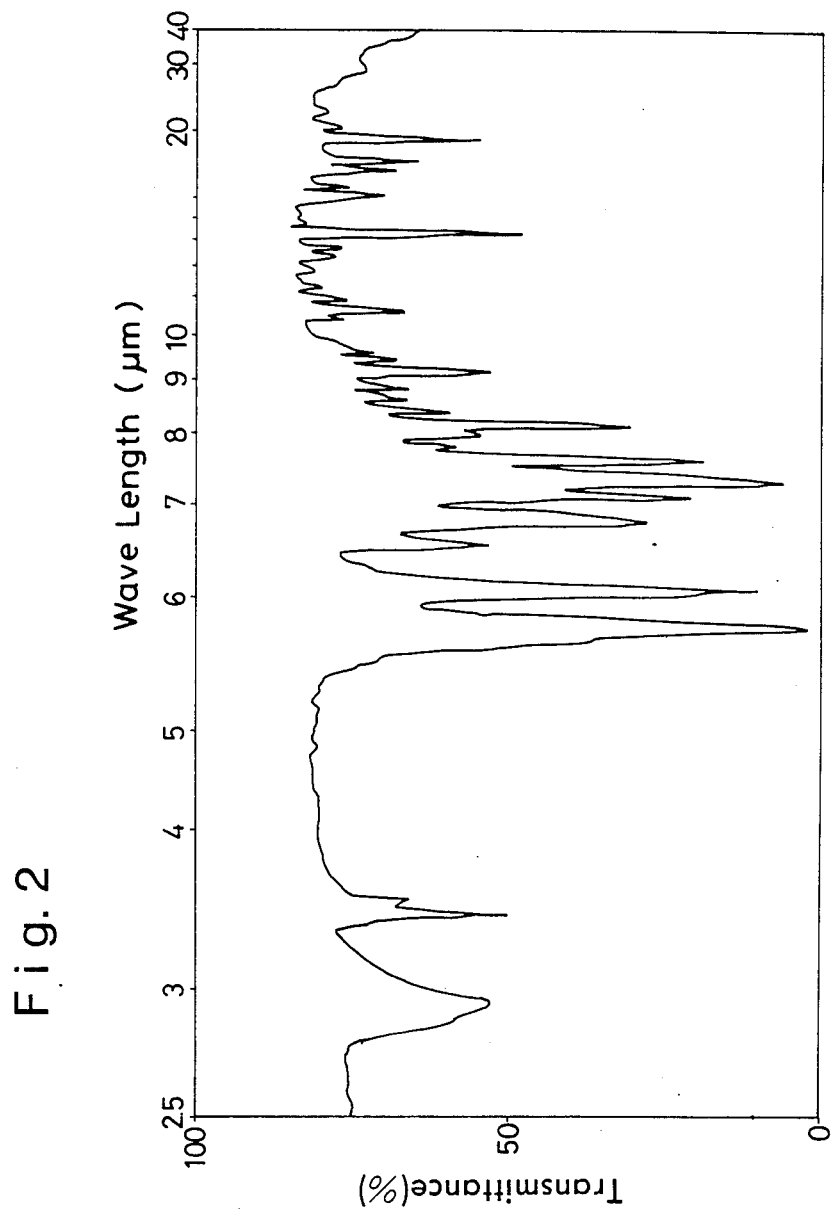
Figure 3:
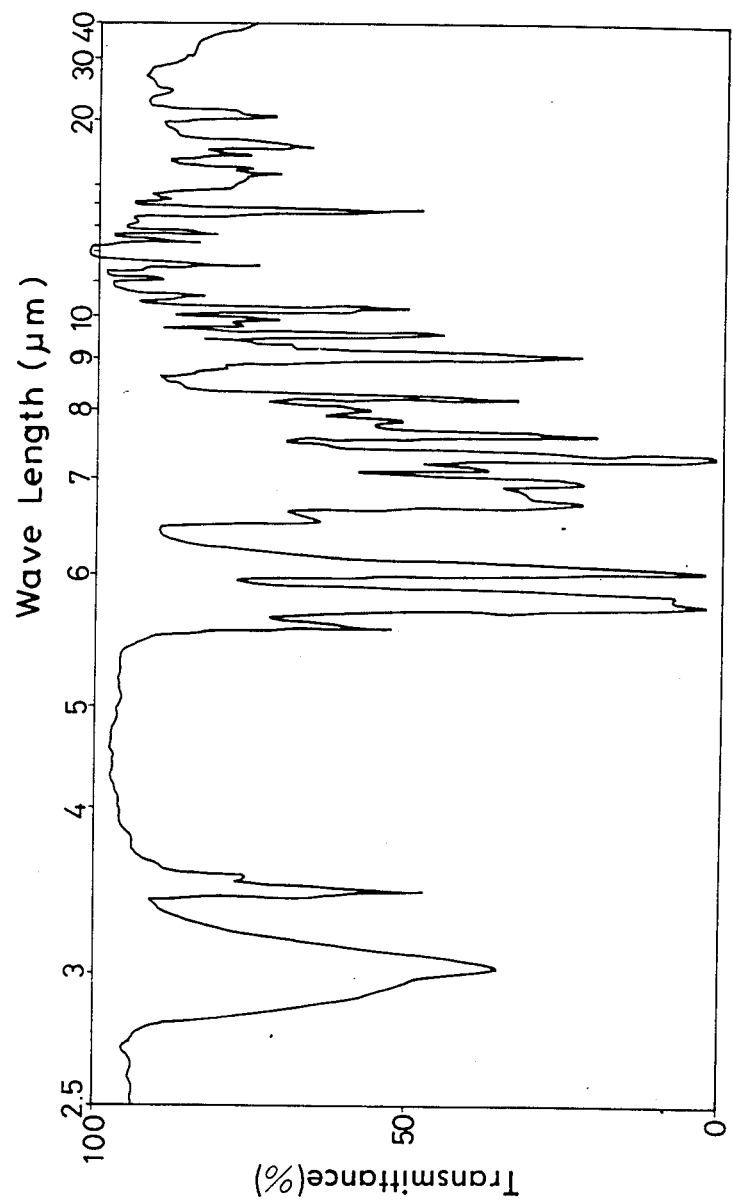

| Compound number | | Melting point (°C.) | Yield (%) | IR spectrum |
|---|---|---|---|---|
| 1 | HO  OH<br>−N    N−CH₂CH₃<br>‖<br>O | 175–177 | 57 | FIG. 1 |
| 2 | O=  =O<br>−N    N−CH₂CH₃<br>‖<br>O | 165–167 | 57 | FIG. 2 |
| 3 | O=  OH<br>−N    N−CH₃<br>‖<br>O | 230–231 | 45 | FIG. 3 |

TABLE 1-continued

Structure: R¹−C(R²)(X)−N... N−R ring with C=O

Figure 4:
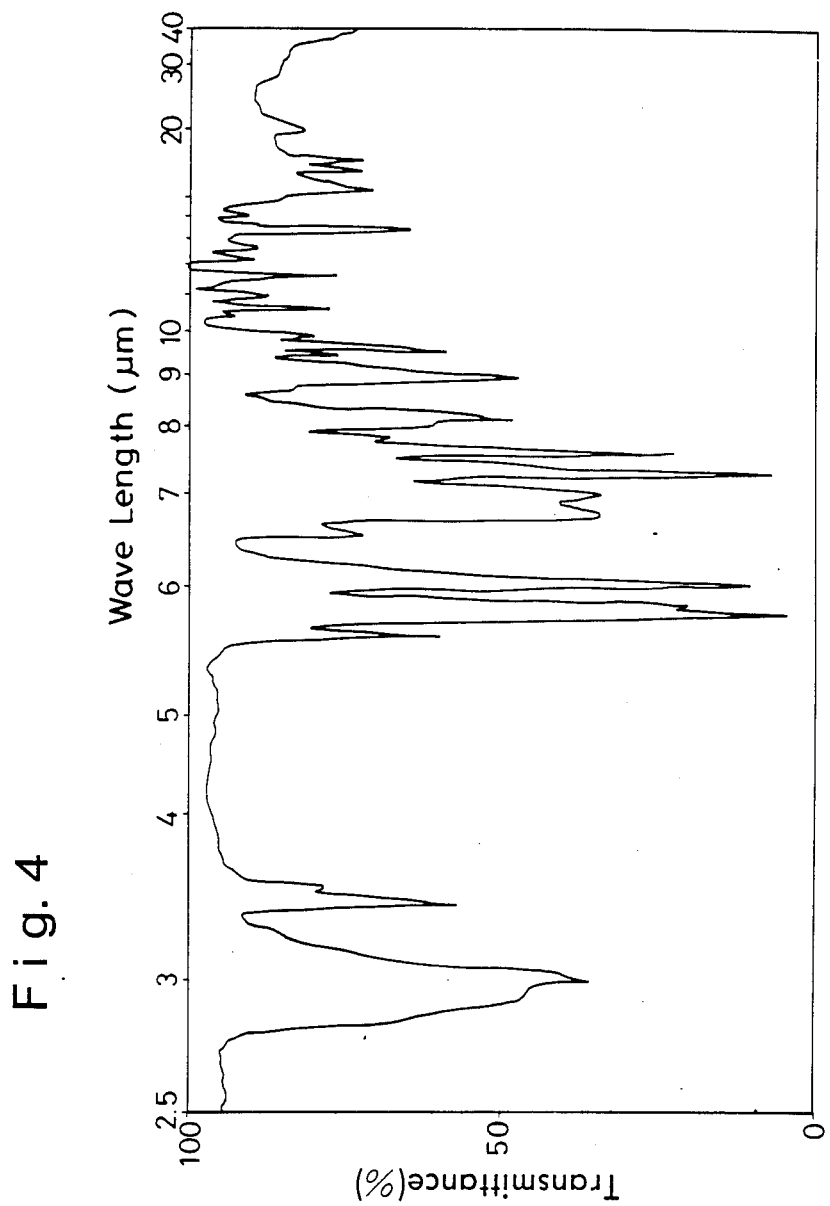
Figure 5:
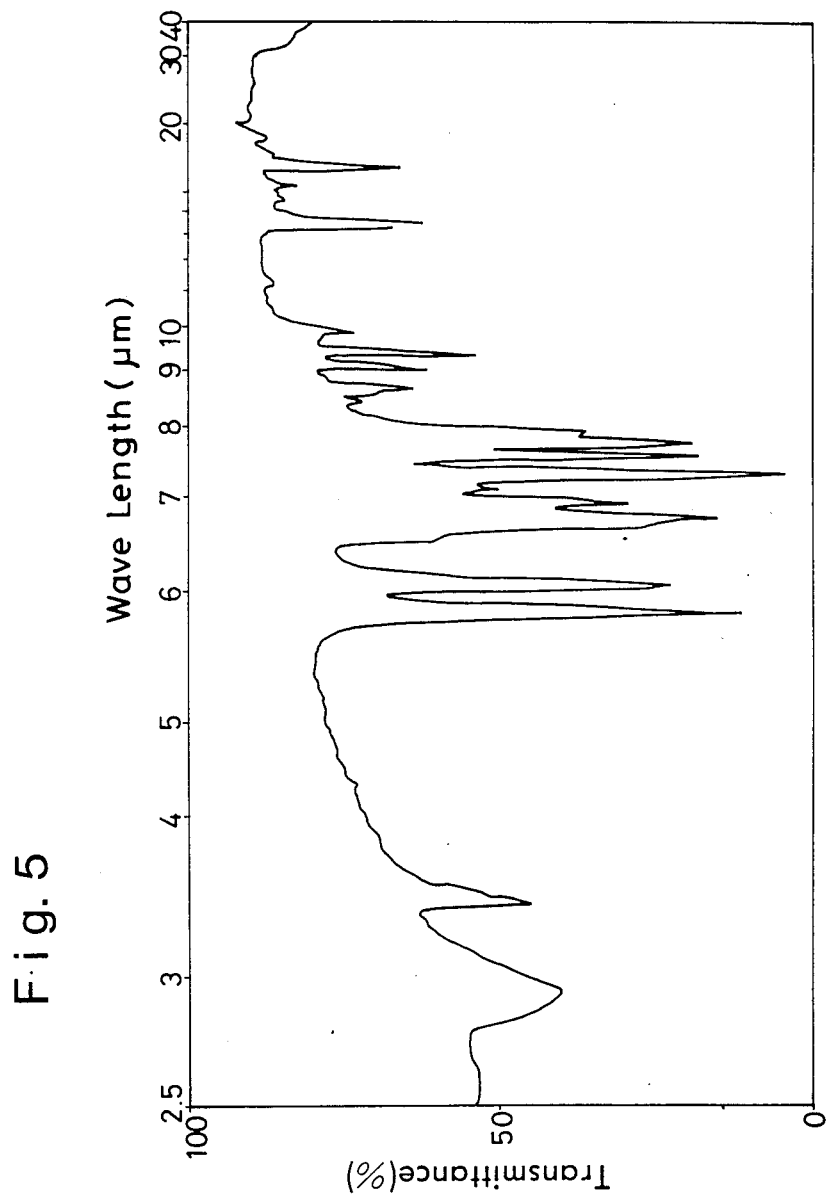
Figure 6:
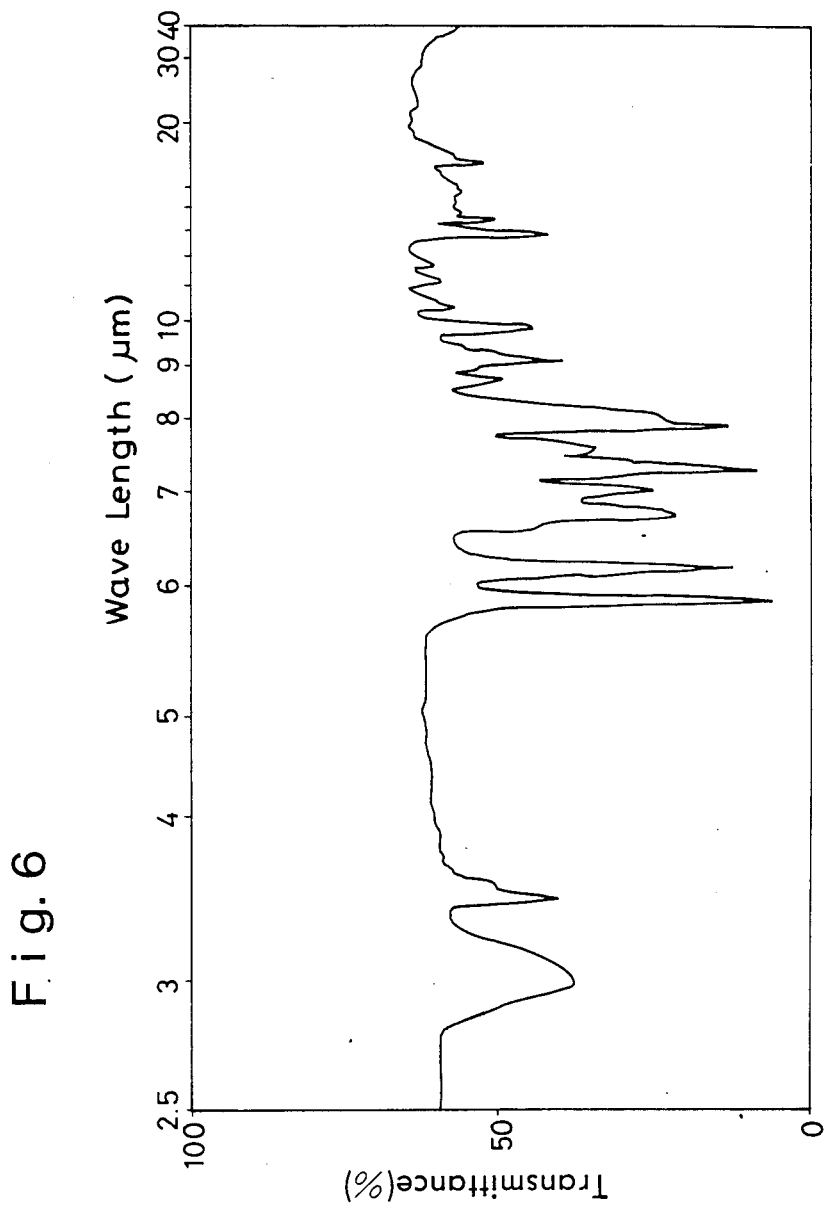
Figure 7:
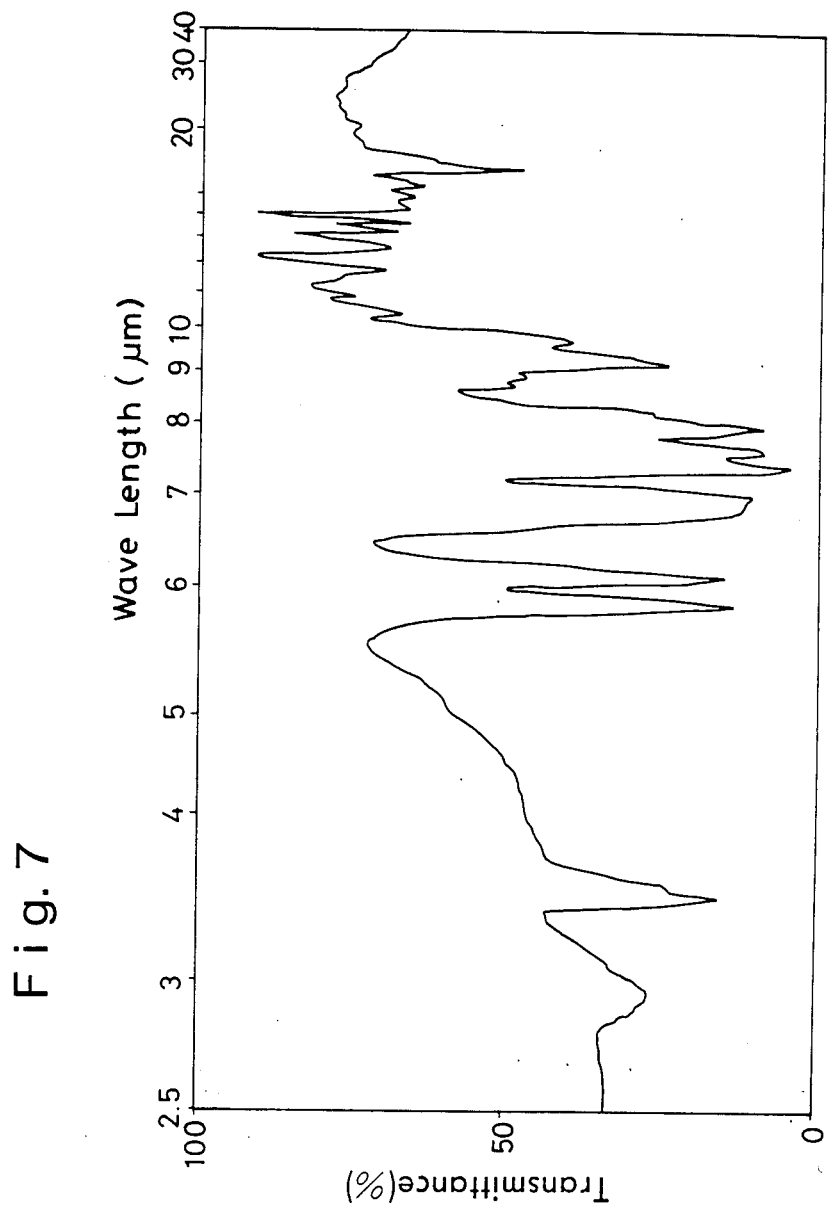
Figure 8:
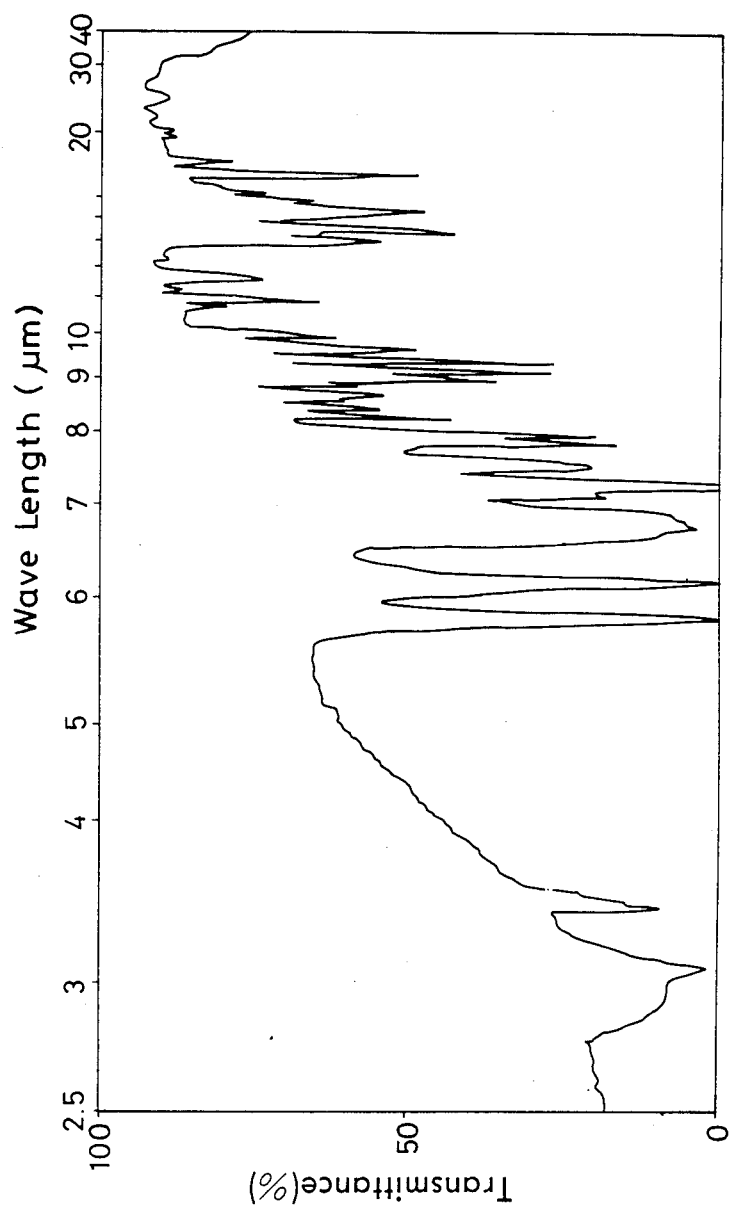
Figure 9:
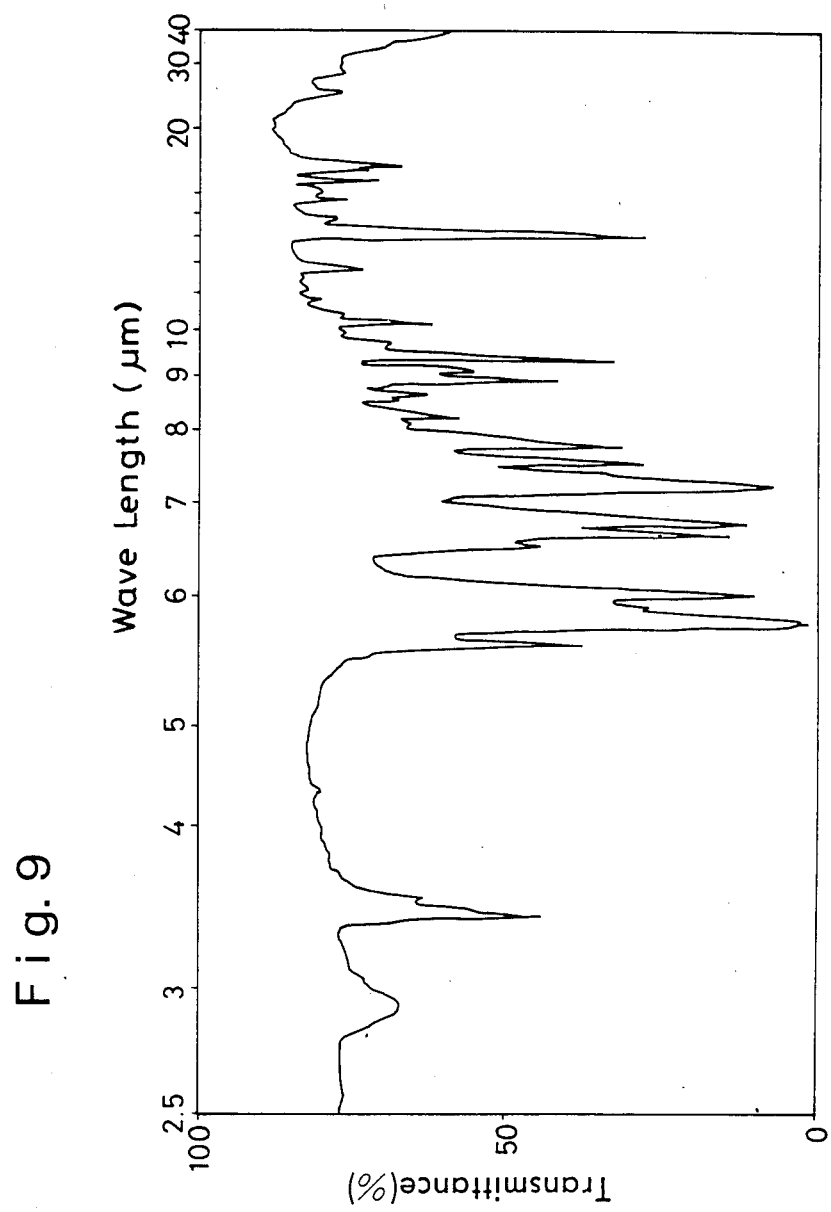
Figure 10:
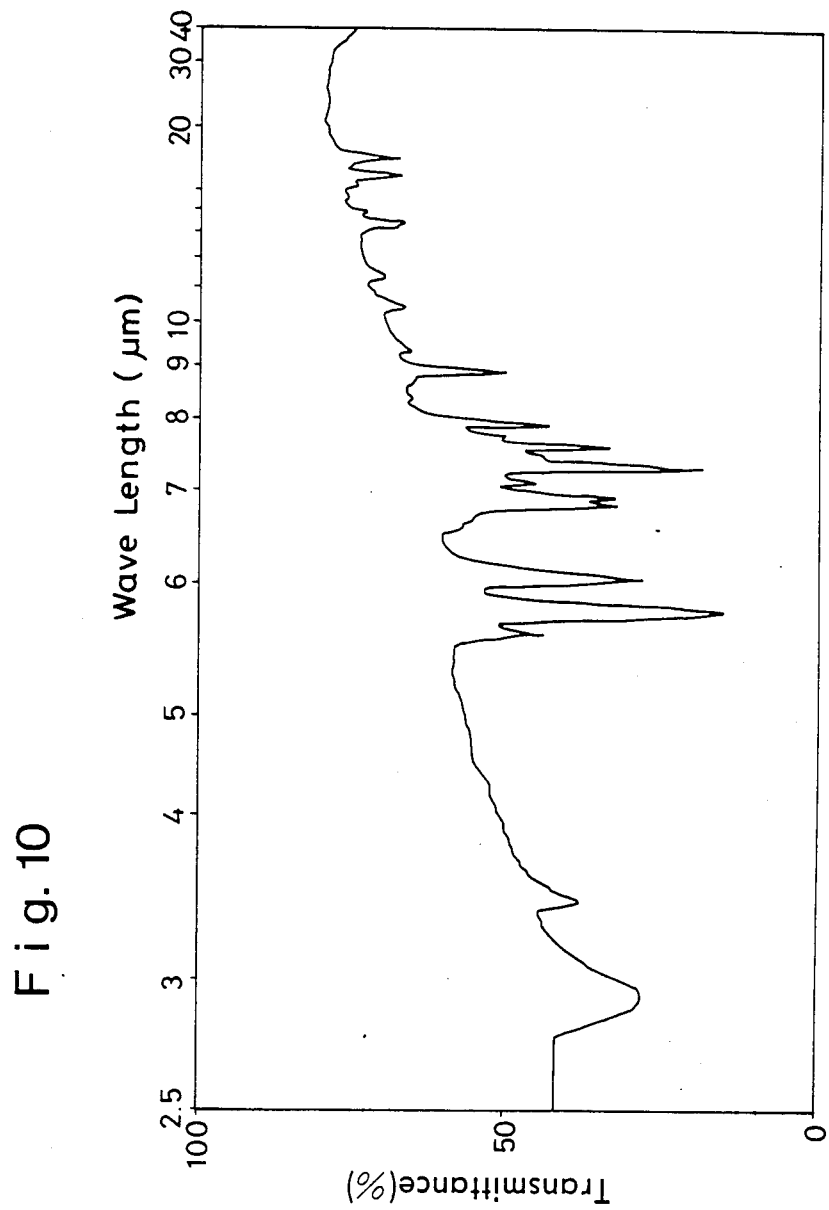
Figure 11:
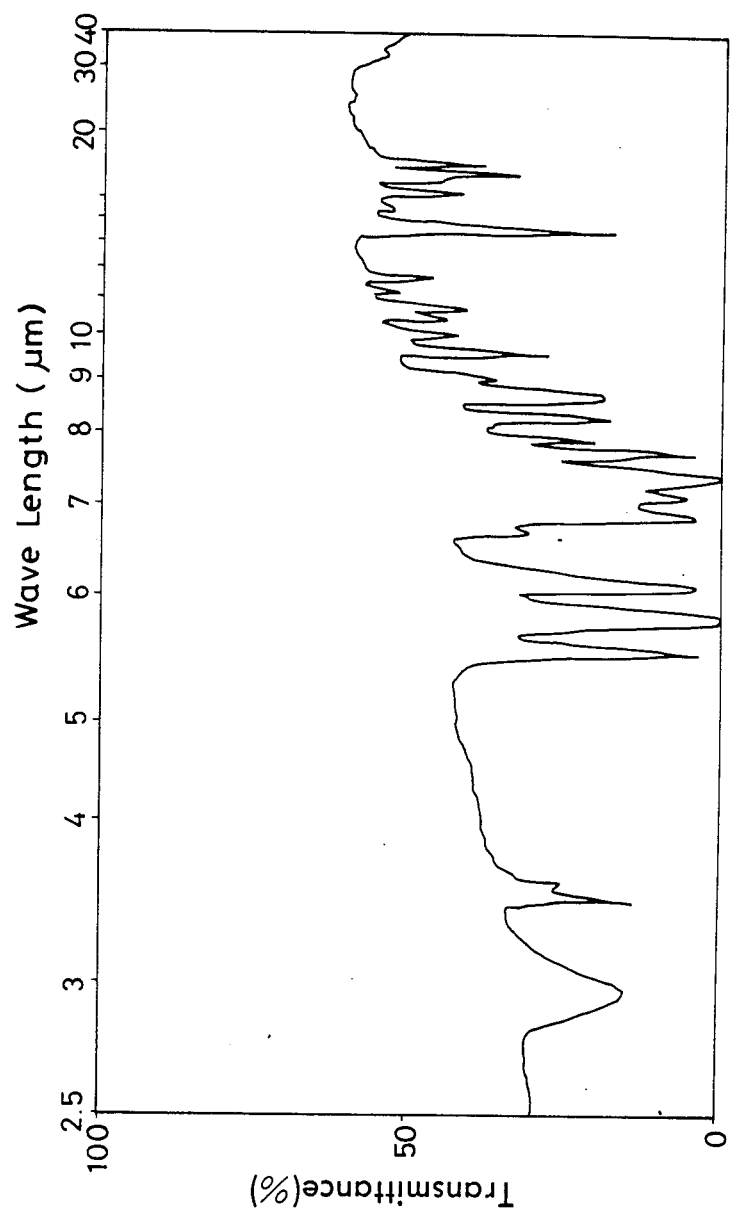

| Compound number | Structure | Melting point (°C.) | Yield (%) | IR spectrum |
|---|---|---|---|---|
| 4 | O=, OH substituents; N−CH₂CH₃ | 213–214 | 60 | FIG. 4 |
| 5 | N−CH₃ | 185–186 | 19 | FIG. 5 |
| 6 | HO substituent; N−CH₂CH₃ | 220–222 | 73 | FIG. 6 |
| 7 | CH₃O substituent; N−CH₂CH₃ | 130–132 | 85 | FIG. 7 |
| 8 | OH substituent; N−CH₃ | 175–176 | 42 | FIG. 8 |
| 9 | =O substituent; N−CH₃ | 184–186 | 46 | FIG. 9 |
| 10 | O= substituent; N−CH₃ | 158–160 | 38 | FIG. 10 |
| 11 | O=, O substituents; N−CH₃ | 145–147 | 24 | FIG. 11 |

The present invention will be more precisely explained while referring to examples as follows.

However, the present invention is not restricted to examples under mentioned.

In addition, the NMR spectra of the present compounds were determined by utilizing TMS as the internal standard, and shown by the following indexes. S: singlet; d: doublet; t: triplet; 6-plet: sextet and m: multiplet.

EXAMPLE 1

Synthesis of 1-ethyl-3-(4,5,6,7-tetrahydro-5,5-dimethyl-7-oxo-2-benzothiazolyl)-imidazolidinetrione (Compound No. 2)

Into 20 ml of dichloromethane, 2.5 g (0.009 mol) of N-(4,5,6,7-tetrahydro-5,5-dimethyl-7-oxo-2-benzothiazolyl-N'-ethylurea were added, and 1.3 g (0.01 mol) of oxalyl chloride was added dropwise to the mixture at room temperature. After heating the mixture under reflux for one hour, 30 ml of n-hexane were added to the reaction mixture, and the thus precipitated crystals were collected by filtration and washed with water. Then, the washed crystals were recrystallized from ethanol to obtain 1.7 g of whity crystals (yield: 57% and M.P.: 165° to 167° C.). The product showed the following IR spectrum and NMR spectrum.

IR (KBr, cm$^{-1}$): $\nu_{CO}$ 1780, 1750 and 1655.

NMR (DMSO-d$_6$)δ(ppm): 1.10 [6H, S, 5'-(CH$_3$)$_2$]; 1.21 (3H, t, J=7 Hz, CH$_2$CH$_3$); 2.51 and 2.92 (each 2H, each S, 4'-H$_2$ and 6'-H$_2$) and 3.68 (2H, q, J=7 Hz, CH$_2$CH$_3$).

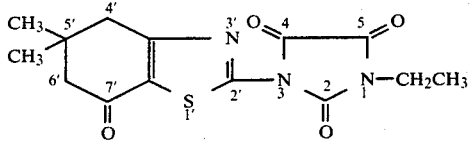

EXAMPLE 2

Synthesis of 3-(4,5,6,7-tetrahydro-5,5-dimethyl-7-oxo-2-benzothiazolyl)-5-hydroxy-1-methyl-2,4-imidazolidinedione (Compound No. 3)

In 25 ml of benzene, 2.5 g (0.01 mol) of N-(4,5,6,7-tetrahydro-5,5-dimethyl-7-oxo-2-benzothiazolyl)-N'-methylurea and 1.2 g (0.013 mol) of glyoxylic acid monohydrate were suspended, and the suspension was heated under reflux while removing water by azeotropic distillation for 2 hours. Then the residue was cooled to collect the crystals by filtration, and the crystals were washed with benzene and then with water, and recrystallized from a mixture of acetone and ethanol to obtain 1.4 g of whity crystals [yield: 45% and M.P.: 230° to 231° C. (decomposition)]. The product showed the following IR spectrum and NMR spectrum.

IR (KBr, cm$^{-1}$): $\nu_{OH}$3310, $\nu_{CO}$1809, 1750 and 1650.

NMR (DMSO-d$_6$)δ(ppm): 1.09 [6H, S, 5'-(CH$_3$)$_2$]; 2.51 and 2.91 (each 2H, each S, 4'-H$_2$ and 6'-H$_2$); 2.97 (3H, S, 1-CH$_3$); 5.23 (1H, d, J=9 Hz, 5-H) and 7.49 (1H, d, J=9 Hz, OH).

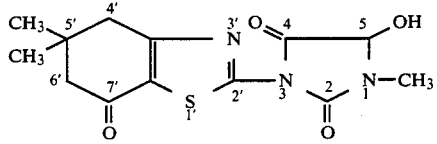

EXAMPLE 3

Synthesis of 1-(4,5,6,7-tetrahydro-5,5-dimethyl-7-oxo-2-benzothiazolyl)-3-methyl-2-imidazolidinone (Compound No. 5)

Into 5 ml of dimethylformamide, 0.7 g (0.003 mol) of 5,5-dimethyl-2-(2-methylaminoethylamino)-4,5,6,7-tetrahydro-7-oxo-2-benzothiazole and 0.85 g (0.005 mol) of carbonyldiimidazole were added, and the mixture was stirred for 3 hours at 80° to 90° C. Then, the reaction mixture was poured into iced water, and the aqueous mixture was extracted with ethyl acetate. After purifying the extract by silica-gel chromatograph, the thus obtained crystals were recrystallized from a mixture of hexane and ethyl acetate to obtain 0.15 g of crystals (yield: 19% and M.P.: 185° to 186° C.). The product showed the following IR spectrum and NMR spectrum.

IR (KBr, cm$^{-1}$): $\nu_{CO}$ 1720 and 1650.

NMR (DMSO-d$_6$)δ(ppm): 1.03 [6H, S, 5'-(CH$_3$)$_2$]; 2.37 and 2.73 (each 2H, each S, 4'-H$_2$ and 6'-H$_2$); 2.85 (3H, S, 3-CH$_3$); 3.28–3.82 (2H, m, 4-H$_2$) and 3.82–4.25 (2H, m, 5-H$_2$).

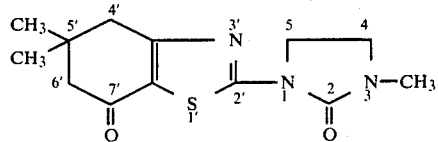

EXAMPLE 4

Synthesis of 1-ethyl-3-(4,5,6,7-tetrahydro-5,5-dimethyl-7-oxo-2-benzothiazolyl)-4-hydroxy-2-imidazolinone (Compound No. 6)

Into 50 ml of aqueous 5% solution of sulfuric acid, 4.3 g (0.012 mol) of N-ethyl-N'-(4,5,6,7-tetrahydro-5,5-dimethyl-7-oxo-2-benzothiazolyl)-N-(2,2-dimethoxyethyl) urea were added, and the mixture was stirred for one hour at 80° to 90° C. After cooling the reaction mixture, the precipitated crystals were collected by filtration and washed with water. By recrystallizing the crystals from methanol containing 20% of water, 2.7 g of white acicular crystals [yield: 73% and M.P.: 220° to 222° C. (decomposition)] were obtained. The product showed the following IR spectrum and NMR spectrum.

IR (KBr, cm$^{-1}$): $\nu_{OH}$ 3400, $\nu_{CO}$ 1710 and 1630.

NMR (CDCl$_3$)δ(ppm): 1.10 [6H, S, 5'-(CH$_3$)$_2$]; 1.21 (3H, t, J=7 Hz, CH$_2$CH$_3$); 2.43 and 2.73 (each 2H, each S, 4'-H$_2$ and 6'-H$_2$); 3.27–3.98 (4H, m, 5-H$_2$ and CH$_2$CH$_3$); 4.99 (1H, bS, OH); and 6.11 (1H, bd, J=6 Hz, 4-H).

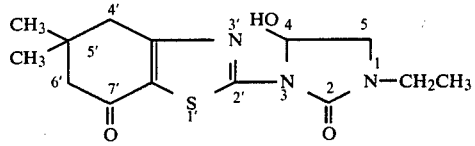

EXAMPLE 5

Synthesis of 1-(4,5,6,7-tetrahydro-5,5-dimethyl-7-oxo-2-benzothiazolyl)-4-hydroxy-3-methyl-2-imidazolinone (Compound No. 8)

Into a mixture of 10 ml of ethanol, 10 ml of water and 2.5 ml of concentrated hydrochloric acid, 1.8 g of N-(4,5,6,7-tetrahydro-5,5-dimethyl-7-oxo-2-benzothiazolyl)-N-(2,2-dimethoxyethyl)-N'-methylurea was added, and the mixture was heated under reflux for 30 min. After distilling ethanol off from the reaction mixture, water was poured to the residue, and the mixture was extracted with ethyl acetate. After washing the organic layer with water and then with aqueous solution of sodium hydrogen carbonate, and drying the washed layer, the solvent was distilled off, and the residue was purified by silica-gel column chromatograph, and recrystallized from benzene to obtain 0.65 g of crystals (yield: 42% and M.P.: 175° to 176° C.). The product showed the following IR spectrum and NMR spectrum.

IR (KBr, cm$^{-1}$): $\nu_{OH}$ 3270, $\nu_{CO}$ 1720 and 1620.

NMR (acetone-d$_6$)$\delta$(ppm): 1.12 [6H, S, 5'-(CH$_3$)$_2$]; 2.40 and 2.77 (each 2H, each S, 4'-H$_2$ and 6'-H$_2$); 2.97 (3H, S, 3-CH$_3$); 3.97 (1H, dd, J=6, 8 Hz, 5-H); 4.30 (1H, dd, J=6, 12 Hz, 5-H); 5.38 (1H, ddd, J=6, 8, 12 Hz, 4-H) and 5.67 (1H, dd, J=6, 8 Hz, OH).

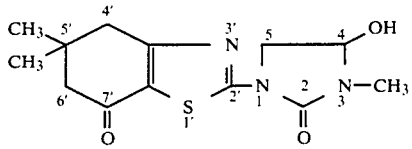

EXAMPLE 6

Synthesis of 1-(4,5,6,7-tetrahydro-5,5-dimethyl-7-oxo-2-benzothiazolyl)-3-methyl-2,4-imidazolinedione (Compound No. 9)

In 5 ml of dimethylformamide, 0.5 g (0.0019 mol) of (4,5,6,7-tetrahydro-5,5-dimethyl-7-oxo-2-benzothiazolyl)amino-N'-methylacetamide and 0.6 g (0.0037 mol) of carbonyldiimidazole were added, and the mixture was stirred for 30 min at room temperature. Then the mixture was poured into iced water, and extracted with dichloromethane. After washing the organic layer with water and drying thereof, the solvent was distilled off from the extract and the residual solid material was recrystallized from a mixture of dichloromethane and ether to obtain 0.25 g of white crystals (yield: 46% and M.P.: 184° to 186° C.). The product showed the following IR spectrum and NMR spectrum.

IR (KBr, cm$^{-1}$): $\nu_{CO}$ 1780, 1720 and 1650.

NMR (DMSO-d$_6$)$\delta$(ppm): 1.10 [6H, S, 5'-(CH$_3$)$_2$]; 2.44 and 2.80 (each 2H, each S, 4'-H and 6'-H); 3.00 (3H, S, 3-CH$_3$) and 4.57 (2H, S, 5-H$_2$).

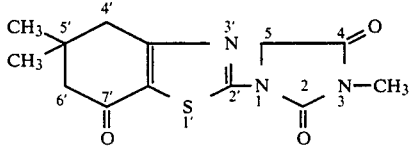

EXAMPLE 7

Synthesis of 3-(4,5,6,7-tetrahydro-5,5-dimethyl-7-oxo-2-benzothiazolyl)-1-methyl-2,4-imidazolidinedione (Compound No. 10)

After heating 0.5 g of N-(4,5,6,7-tetrahydro-5,5-dimethyl-7-oxo-2-benzothiazolyl)carbamoyl-N-methylglycine in 10 ml of acetic anhydride under reflux for 2 hours, the reaction mixture was evaporated to solid.

The thus obtained solid material was recrystallized from a mixture of chloroform and hexane to obtain 0.18 g of pale yellow crystals (yield: 38% and M.P.: 158° to 160° C.). The product showed the following IR spectrum and NMR spectrum.

IR (KBr, cm$^{-1}$): $\nu_{CO}$ 1790, 1735 and 1650.

NMR (CDCl$_3$)$\delta$(ppm): 1.16 [6H, S, 5'-(CH$_3$)$_2$]; 2.52 and 3.05 (each 2H, each S, 4'-H and 6'-H); 3.21 (3H, S, 1-CH$_3$) and 4.28 (2H, S, 5-H$_2$).

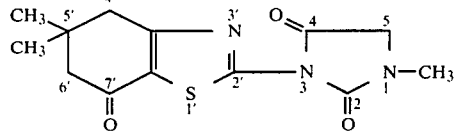

EXAMPLE 8

Synthesis of 4-(4,5,6,7-tetrahydro-5,5-dimethyl-7-oxo-2-benzothiazolyl)-2-methyl-1,2,4-oxadiazolidine-3,5-dione (Compound No. 11)

Into 20 ml of dimethylformamide, 0.4 g (0.0015 mol) of N-(4,5,6,7-tetrahydro-5,5-dimethyl-7-oxo-2-benzothiazolyl)-N'-hydroxy-N'-methylurea and 0.8 g (0.005 mol) of carbonyldiimidazole were added, and the mixture was stirred for 30 min at room temperature and then poured into iced water. The aqueous mixture was extracted with chloroform, and the organic layer was washed with water and dried. After distilling the solvent off from the dried extract, the residual solid material was purified by silica-gel chromatography and recrystallized from a mixture of chloroform and hexane to obtain 0.1 g of white crystals (yield: 24% and M.P.: 145° to 147° C.). The product showed the following IR spectrum and NMR spectrum.

IR (KBr, cm$^{-1}$): $\nu_{CO}$ 1840, 1745 and 1660.

NMR (CDCl$_3$)$\delta$(ppm): 1.15 [6 H, S, 5'-(CH$_3$)$_2$]; 2.50 and 2.97 (each 2H, each S, 4'-H$_2$ and 6'-H$_2$) and 3.54 (3H, S, 2-CH$_3$).

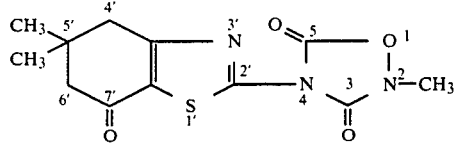

PREPARATION EXAMPLE 1

Preparation and Application of a Wettable Powder

By mixing 50 parts by weight of the present compound (Compound No. 3), 5 parts by weight of a salt of ligninsulfonic acid, 3 parts by weight of a salt of alkylsulfonic acid and 42 parts by weight of diatomaceous earth and pulverizing the mixture, a wettable powder was prepared.

The thus prepared wettable powder is applied after diluting with water to a suitable concentration of the present compound (Compound No. 3) as an active ingredient.

PREPARATION EXAMPLE 2

Preparation and Application of an Emulsifiable Concentrate

By uniformly mixing 25 parts by weight of the present compound (Compound No. 5), 65 parts by weight of xylene and 10 parts by weight of polyoxyethylenealkyl aryl ether, an emulsifiable concentrate was prepared.

The thus prepared emulsifiable concentrate is applied after diluting with water to a suitable concentration of the present compound (Compound No. 5) as an active ingredient.

the present wettable powder was applied being in the 2 to 4 leaf-stage of the growth.

TABLE 2

| | Herbicidal Activity | | | | | | | | | | | None treated |
|---|---|---|---|---|---|---|---|---|---|---|---|---|
| Plant | Number of present compounds | | | | | | | | | | | |
| | 1 | 2 | 3 | 4 | 5 | 6 | 7 | 8 | 9 | 10 | 11 | |
| *Echinochloa crus-galli* | 3 | 1 | 3 | 1 | 3 | 2 | 0 | 0 | 0 | 1 | 1 | 0 |
| *Digitaria ciliaris* | 3 | 1 | 2 | 1 | 2 | 3 | 1 | 1 | 1 | 2 | 2 | 0 |
| *Poa annua* | 3 | 0 | 1 | 0 | 4 | 4 | 2 | 1 | 0 | 1 | 3 | 0 |
| *Cyperus iria* | 2 | 0 | 2 | 2 | 3 | 4 | 0 | 0 | 1 | 0 | 2 | 0 |
| *Chenopodium album* | 4 | 2 | 5 | 3 | 5 | 3 | 3 | 4 | 3 | 4 | 5 | 0 |
| *Stellaria media* | 4 | 3 | 5 | 3 | 5 | 4 | 4 | 4 | 2 | 5 | 5 | 0 |
| *Cardamine flexuosa* | 5 | 3 | 5 | 4 | 5 | 5 | 3 | 4 | 3 | 5 | 5 | 0 |
| *Portulaca oleracea* | 4 | 3 | 4 | 3 | 5 | 3 | 3 | 5 | 2 | 4 | 5 | 0 |
| *Glycine max* (soybean) | 0 | 0 | 0 | 0 | 1 | 0 | 0 | 0 | 0 | 0 | 0 | 0 |
| *Zea mays* (maize) | 0 | 0 | 0 | 0 | 0 | 0 | 0 | 0 | 0 | 0 | 0 | 0 |
| *Triticum aestivum* (wheat) | 0 | 0 | 0 | 0 | 0 | 0 | 0 | 0 | 0 | 0 | 1 | 0 |

PREPARATION EXAMPLE 3

Preparation and Application of a Granular Composition

After uniformly mixing 8 parts by weight of the present compound (Compound No. 11), 40 parts by weight of bentonite, 45 parts by weight of clay and 7 parts by weight of a salt of ligninsulfonic acid, the mixture was kneaded with water and processed into granules by an extruding granulator. The granules were dried and shifted to be a product of granular composition which is directly applied.

The effectiveness of the present compounds are explained while referring to the herbicidal test example as follows:

HERBICIDAL TEST EXAMPLE

Herbicidal Test Example by Foliar Application

To the foliage of each of the following plants grown from their seeds under a management in a plastic planter of 180×580×150 mm in size, each of the wettable powders prepared by the same method as in Preparation Example 1 and diluted to 0.1% by weight of the active ingredient with water was sprayed by a small pressured-sprayer at a rate of 10 liters per are (100 m²). After spraying the plastic planter were placed in a green house.

After 21 days of the treatment, the state of the plants was observed to assess the damage due to the application of each of the wettable powders and the herbicidal activity thereof was judged according to the following criteria.

| Criteria of herbicidal activity | |
|---|---|
| Index | Phytotoxicity |
| 0 | none |
| 1 | minute |
| 2 | slight |
| 3 | medium |
| 4 | severe |
| 5 | very severe (withered) |

| Name of the plants tested | |
|---|---|
| 1. *Echinochloa crus-galli* | 2. *Digitaria ciliaris* |
| 3. *Poa annua* | 4. *Cyperus iria* |
| 5. *Chenopodium album* | 6. *Stellaria media* |
| 7. *Cardamine flexuosa* | 8. *Portulaca oleracea* |
| 9. *Glycine max* (Soybean) | 10. *Zea mays* (Maize) |
| 11. *Triticum aestivum* (Wheat) | |

The herbicidal activities of the present compounds thus assessed are shown in Table 2, the plants to which

What is claimed is:

1. A derivative of tetrahydrobenzothiazole represented by the formula (I):

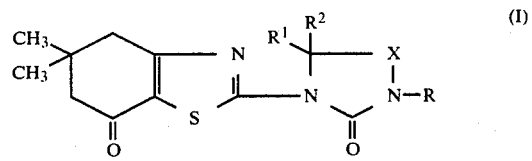

wherein R represents a methyl group or ethyl group; $R^1$ represents a hydrogen atom, a hydroxyl group, methoxy group or =O together with $R^2$; $R^2$ represents a hydrogen atom or =O together with $R^1$ and X represents a methylene group, hydroxymethylene group, carbonyl group —O—, with the proviso that (1) X is not a methylene group when $R^1$ represents a methoxy group, (2) X is not a carbonyl group when $R^1$ represents =O together with $R^2$, (3) R is not an ethyl group when $R^1$ represents =O together with $R^2$ and X represents a hydroxymethylene group and (4) R is not a methyl group when $R^1$ represents a hydroxyl group and X represents a methylene group or a hydroxymethylene group, when $R^1$ represents a methoxy group and X represents a hydroxymethylene group, or when $R^1$ represents a hydrogen atom and X represents a carbonyl group; wherein the imidazolidinone moiety of said derivative is one selected from the group consisting of

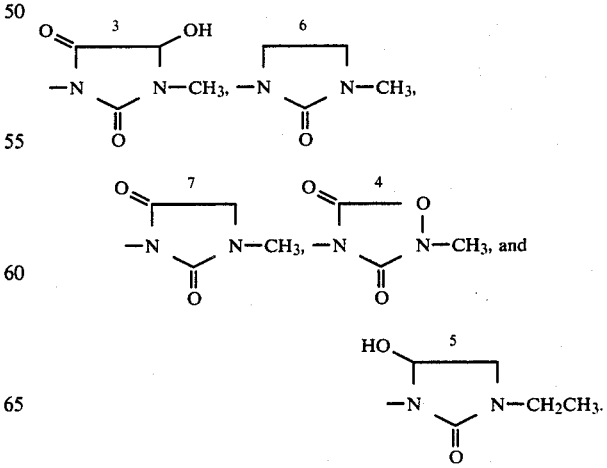

2. A herbicidal composition comprising at least one of the derivatives of tetrahydrobenzothiazole, represented by the formula (I):

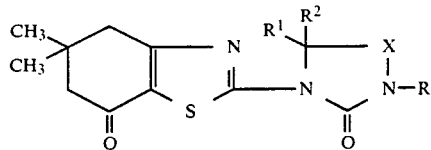

wherein R represents a methyl group or ethyl group; $R^1$ represents a hydrogen atom, a hydroxyl group, methoxy group or =O together with $R^2$; $R^2$ represents a hydrogen atom or =O together with $R^1$ and X represents a methylene group, hydroxymethylene group, carbonyl group or —O—, with the proviso that (1) X is not a methylene group when $R^1$ represents a methoxy group, (2) X is not a carbonyl group when $R^1$ represents =O together with $R^2$, (3) R is not an ethyl group when $R^1$ represents =O together with $R^2$, and X represents a hydroxymethylene group and (4) R is not a methyl group when $R^1$H represents a hydroxyl group and X represents a methylene group or a hydroxymethylene group, when $R^1$ represents a methoxy group and X represents a hydroxymethylene group, or when $R^1$ represents a hydrogen atom and X represents a carbonyl group; wherein the imidazolidine moiety of said derivative is one selected from the group consisting of

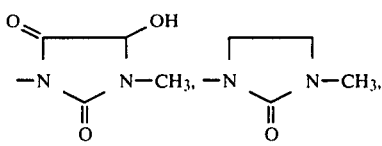

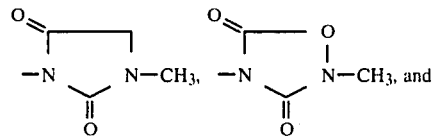

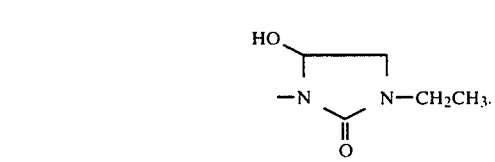

* * * * *